United States Patent [19]

Schetters

[11] Patent Number: 6,045,806

[45] Date of Patent: *Apr. 4, 2000

[54] BABESIA VACCINE

[75] Inventor: Theodorus Petrus Maria Schetters, Cuyk, Netherlands

[73] Assignee: Akzo Nobel N.V., Arnhem, Netherlands

[ * ] Notice: This patent issued on a continued prosecution application filed under 37 CFR 1.53(d), and is subject to the twenty year patent term provisions of 35 U.S.C. 154(a)(2).

[21] Appl. No.: 08/498,550

[22] Filed: Jul. 5, 1995

[30] Foreign Application Priority Data

Jul. 6, 1994 [EP] European Pat. Off. .............. 94201944

[51] Int. Cl.$^7$ .................................................. A61K 39/018
[52] U.S. Cl. ...................................... 424/270.1; 424/265.1
[58] Field of Search ............................... 424/265.1, 270.1

[56] References Cited

U.S. PATENT DOCUMENTS 4,777,036 10/1988 Laurent ...................................... 424/88

FOREIGN PATENT DOCUMENTS 0018579 11/1980 European Pat. Off. .
0220988 5/1987 European Pat. Off. .

OTHER PUBLICATIONS

G. Uilenberg et al., "Three Groups of Babesia Canis Distinguished and a proposal for nomenclature," Biological Abstracts, 88:2:abstract 16375, 1989, Philadelphia PA, USA.

*Primary Examiner*—David Saunders
*Assistant Examiner*—Mary Beth Tung
*Attorney, Agent, or Firm*—Michael G. Sullivan; William M. Blackstone

[57] ABSTRACT

The invention is directed to a vaccine comprising *Babesia canis* antigens from a strain of *Babesia canis rossi* and another *Babesia canis* subspecies.

Such a vaccine gives both homologous protection, and heterologous protection to infection with strains other than those of which the antigens have been isolated.

Preferably the antigens are soluble antigens which can be harvested from the supernatant of a culture of Babesia parasites.

3 Claims, 4 Drawing Sheets

Vaccination against Babesia canis induction of heterologous immunity

□ B.canis A+B.rossi   + control

FIG. 6

Vaccination against Babesia canis induction of heterologous immunity

◊ A+rossi
△ control time relative to challenge infection

FIG. 7

BABESIA VACCINE

This invention is related to a vaccine against babesiosis, more specifically against canine babesiosis.

Babesiosis, like malaria, is a disease which has a focal character. The reason for this is that the pathogen is transmitted by ticks that feed on a certain reservoir of parasites present in the vertebrate population. Only where ticks are present, babesiosis can occur. On balance, particularly in indigenous animals, the parasite coexists with the host without causing significant disease. In many cases babesiosis is a problem because of man's activities through inbreeding of genetic traits and/or transporting animals to unfamiliar environments where babesiosis is endemic (Callow, L. L and Dalgliesh, R. J., 1982).

In dogs the disease is caused by *Babesia canis* and *Babesia gibsoni*.

At present three subspecies of *B. canis* are distinguished: *B. c. canis* (transmitted by Dermacentor ticks), *B. c. rossi* (transmitted by Haemaphysalis ticks) and *B. c. vogeli* (transmitted by Rhipicephalus ticks; Uilenberg, G. et al., 1989).

Signs of disease in naturally acquired babesiosis usually begin 7–21 days after infection. These symptoms include: fever, anorexia, depression, anaemia, haemoglobinuria and rapidly developing weakness. Increased lacrimation, salivation and muscle tremor commonly occur. Nervous signs may develop in terminal infections, and death may occur when the disease is left untreated. Severe coagulation disturbances resembling disseminated intravascular coagulation (DIC) have been reported in acute B. canis infections (Moore, D. J. and Williams, M. C., 1979). Thrombosis is not common, but small hyaline thrombi, connected with megakaryocytes have been described (Fischer, W. and Scheideman, H., 1920). It appears that these coagulation disturbances lead to increased erythrocyte-stickiness. As a result the blood passage through the microvasculature is hampered, resulting in congestion of internal organs and decreased packed cell volumes (PCV). This might impair the oxygen supply to certain tissues and subsequently lead to tissue damage as a result of anoxia (Malherbe, W. D. and Parkin, B. S., 1951; Basson, P. A. and Pienaar, J. G., 1965; Jacquier, C., 1973). Evidence from congestion in *B. canis* infections comes from experiments in which dogs were chemotherapeutically treated. Some of these animals restore the packed cell volume in two days from 25–35%, which is associated with shrinkage of the spleen to normal measures.

The three subspecies of *B. canis* differ with respect to their pathogenicity (Uilenberg et al., 1989). The North-African *B. c. vogeli* strains provoke only mild disease, which usually does not require treatment (like the Australian *B. canis* strains). European *B. c. canis* strains are more pathogenic than the North-African parasite. In our experiments with the *B. c. canis* A strain, approximately half of the animals required chemotherapeutic treatment after infection (Schetters et al., 1994). The South-African *B. c. rossi* strains are most pathogenic, a feature observed already very early (Nuttal, 1904). Using the South-African *B. c. rossi* strain naive dogs developed progressing disease characterised by exponential parasite growth. In contrast, parasitaemia in dogs infected with European *B. c. canis* usually is limited. In the latter, congestion appears to be the main pathological feature.

At the moment a vaccine for Babesia is prepared from the supernatant of a culture of a strain of *Babesia canis*, as is described in U.S. Pat. No. 4,777,036. However, such a vaccine contains only antigens of this strain of this particular subspecies of *B. canis*. It appears that such a vaccine gives in general little protection against infections with (wild type) *B. canis* (Lepetit, C., Piroplasmose canine et vaccination Pirodog, Doctoral Thesis, Univ. of Nantes, 1988). The author of the thesis gives three possible causes of this failure of protective immunization:

1. the sensitivity of the dogs with respect to vaccination;
2. the type of immune effector mechanism induced by vaccination;
3. the antigenic diversity of Babesia.

Strain dependency of this type of vaccination against *Babesia bovis* in cattle has been shown (Ristic and Montenegro-James, 1988). A similar finding has been made in vaccination of dogs (Sibinovic et al. 1967 and Schetters et al. 1995). Herein it is described that the antigenic diversity of Babesia has a great impact on the efficacy of vaccination: if the vaccine is made from the supernatant of a culture of a single strain of Babesia it only protects against challenges with the homologous strain.

Vaccines containing whole, attenuated Babesia parasites always harbour the danger that the parasites again become virulent and thus spread the disease instead of curing it. Therefore, it is preferable to use a subunit vaccine.

Thus there remains the desire for a vaccine which is not infective, which can be easily produced and which yet can give protection against heterologous (wild-type) challenge infection.

Our invention now is a vaccine for protection against babesiosis comprising antigens from *B. canis*, characterised in that it comprises antigens from *B. canis rossi* and antigens from another *B. canis* subspecies.

Antigens in this respect are biological entities obtainable from Babesia in any way, that are capable of eliciting an immunological response in dogs after administration. Antigens can comprise both somatic parasitic molecules and molecules excreted or secreted by the parasite. Also host molecules altered as a result of infection with Babesia are included in this definition.

Known subspecies of *Babesia canis* next to *B. c. rossi* are *B. c. canis* and *B. c. vogeli* (Uilenberg, G. et al., 1989). From *B. c. canis* at least three different strains have been isolated, denominated strain A, strain B and the strain used in the commercial vaccine 'Pirodog®', (*B. canis canis*, strain robin).

The vaccine according to the invention may comprise an antigen in a pure form, optionally in the presence of a veterinary acceptable carrier. The antigen can optionally be covalently bound to a non-related protein.

Such a vaccine does not only protect against infections with *B. c. canis* strain from which the antigens in the vaccine have been isolated (homologous protection), but it surprisingly also gives protection to infections with heterologous *B. c. canis* strains.

The model of homologous protection has been indicated by Lepetit (supra), and is demonstrated by our experiments in which vaccination with antigens from subspecies *B. c. canis* strain A does not protect against infections with *B. c. canis* strain B (Schetters et al., 1995). Also vaccination with Pirodog® (commercially available and produced from a culture of another *B. c. canis* subspecies strain) does not protect against challenge with either *B. c. canis* strain A or *B. c. canis* strain B. Furthermore, vaccination with antigens of a strain of *B. c. rossi* alone is—in contrast to the findings after infection with a wild-type strain—not protective for challenges with any strain of *B. c. canis*.

From our experiments it surprisingly appeared that vaccination with a vaccine comprising both antigens from supernatants of cultures of *B. c. rossi* and *B. c. canis* strain A gave adequate protection upon challenge with *B. c. canis* strain B parasites. This means that such a vaccine enables heterologous protection.

Preferably the vaccine is prepared from soluble antigens which are released in the medium of a culture of Babesia in for example erythrocytes. For this culture to blood of an infected animal an anticoagulant is added and a cell suspension from this sample is grown in culture flasks on a medium suitable for growth. Soluble antigens, i.e. antigens which do not precipitate in an aqeous solution such as culture medium, are collected.

Preferably the antigens will be derived from the culture supernatant, which is harvested. The antigens can be concentrated by filtering or evaporation of the medium, or any other suitable way.

In addition to an immunogenically effective amount of the antigen the vaccine may contain a pharmaceutically acceptable carrier or diluent. Examples of pharmaceutically acceptable carriers or diluents useful in the present invention include stabilizers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer).

The immunogenicity of the antigens of the invention can be enhanced by cross-linking or by coupling to an immunogenic carrier molecule (i.e. a macromolecule having the property of independently eliciting an immunological response in a recipient, to which the antigens of the invention can be linked, for example β-galactosidase, protein A, prochymosine, blood clotting factor Xa, etc.).

Coupling to the carrier molecule can be carried out using methods well known in the art, the exact choice of which will be dictated by the nature of the antigen and the carrier molecule used. When the immunogenic carrier molecule is a protein, the Babesia antigens can be coupled, e.g. using water soluble carbodiimides such as dicyclohexylcarbodiimide, or glutaraldehyde.

Coupling agents such as these can also be used to cross-link the antigens to themselves without the use of a separate carrier molecule. Such cross-linking into peptide aggregates can also increase immunogenicity.

Optionally, one or more compounds having adjuvant activity may be added to the vaccine. Suitable adjuvants are for example aluminium hydroxide, phosphate or oxide, oil-emulsions (e.g. of Bayol F$^{(R)}$ or Marcol 52$^{(R)}$), or saponins e.g. QuilA$^{(R)}$.

The vaccine according to the present invention can be given inter alia subcutaneously or intramuscularly.

The optimal effective amount to be administered will vary depending on the age and weight of the animal and mode of administration of the vaccine. A suitable dose will be the amount of antigenic material produced by $2.10^7$–$2.10^9$ parasites in 12 hours culturing, of which parasites preferably half is *B. c. rossi* and the other half is an other *B. canis* subspecies.

The method to prepare a vaccine according to the invention will, in general, comprise the steps of culturing the Babesia parasites in a suitable medium;

harvesting the antigenically active substances from this medium;

admixing said substances with pharmaceutically acceptable excipients.

BRIEF DESCRIPTION OF THE DRAWINGS

Legend to the figures.

FIG. 6. The antibody response against *Babesia canis*-infected erythrocytes upon vaccination with a combination vaccine. Data represent end-point titres of pooled serum samples.

FIG. 7. The effect of combination-vaccination on the peripheral red blood cell number after heterologous challenge infection. Data are expressed as packed cell values (PCV) and represent the mean value of groups of animals. No animals were chemotherapeutically treated.

EXAMPLES

Materials and Methods

Animals

Figure 1:
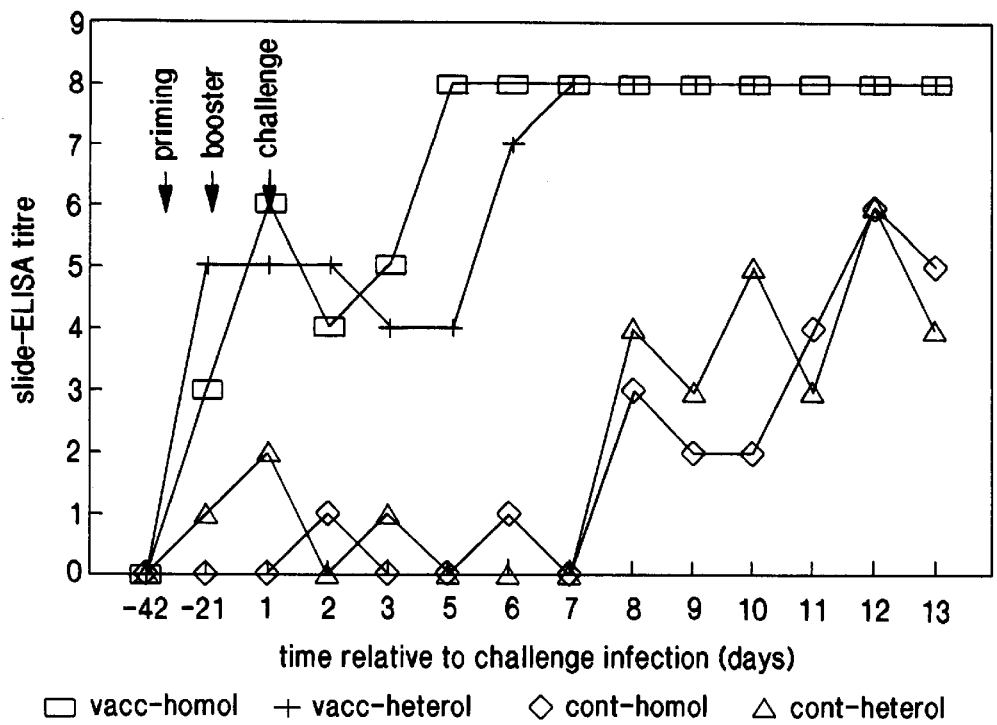
FIG. 1. The development of antibody reactivity against infected erythrocytes upon vaccination with a monovalent vaccine and subsequent challenge infection. Data represent the mean antibody titre as determined in slide-ELISA from groups of animals.

Dogs (Beagle) of approximately 7 months of age and of both sexes were used. They were kept at the dog-unit of Intervet International (Boxmeer, The Netherlands). They received a standard amount of food daily. Drinking water was supplied ad libitum. Experimental groups were formed assuring an equal distribution of animals according to litter and sex.

Parasites

Two different *Babesia canis canis* isolates (A and B) were used. They both originated from France. *Babesia canis rossi* originates from South-Africa (Uilenberg et al., supra). Isolates were stored as stabilate in liquid nitrogen, and passed once through a splenectomised dog before in vitro culture or infection. Challenge infections were done with blood from infected dogs.

Challenge infection

Three weeks after the booster injection with vaccine dogs were challenged with blood of an infected dog. The blood was taken by venapuncture from the vena jugularis using heparin to prevent clotting. The blood was washed once in Babesia medium (see below). A volume of blood, containing $2.10^6$ infected erythrocytes was injected intravenously into recipient dogs.

Parasitaemia

The parasitaemia is expressed as the log number of red blood cells infected with Babesia parasites per $10^5$ erythrocytes in the peripheral blood (taken by venapunction from the vena jugularis according to Jarra and Brown, 1985). It was read from blood smears stained with May-Grunwald/Giemsa solutions.

Haematocrit

The haematocrit value is expressed as packed cell volume (PCV) of a sample of venous blood taken from the vena jugularis. A haematocrit capillary was filled with heparinised blood and centrifuged in a haematocrit centrifuge for 5' at 10,000 rpm. The packed cell volume was read using a haematocrit reader (Hawksley).

Serum

Serum was prepared according to routine procedures. Blood was collected from the vena jugularis and allowed to clot at room temperature for at least 60 minutes. Cellular contaminants were removed by centrifugation (1500 g, 10', room temperature). Serum was stored at $-70°$ C.

Plasma

Plasma was prepared from heparinised blood from the vena jugularis. The sample was kept on ice. Cells were pelleted by centrifugation (1500 g, 10', 4° C.), and the clear plasma aspirated. It was stored at $-70°$ C.

Babesia medium

RPMI-1640 (Gibco), supplemented with HEPES (40 mM), sodiumpyruvate (1 mM), L-glutamine (2 mM) and sodium hydrogen carbonate (1 g/l) was adjusted to pH 7.4, and used for in vitro culture of the parasite In vitro culture The parasite was cultured in vitro for a limited period of time as essentially described (Schetters et al., 1992.). In short, blood of an infected dog was withdrawn by venapuncture, collected in a tube containing heparin to prevent clotting, and immediately put on ice. The blood was washed and a cell suspension of 5% packed cell volume (PCV) and 0.3% parasitaemia was prepared in complete Babesia medium (which contains 40% v/v normal dog serum). A volume of 40 ml was cultured in 75 cm² culture flasks (Greiner). The flasks were gassed with commercial gas mixture containing 2% (v/v) $O_2$, 5% (v/v) $CO_2$ and 93% (v/v) $N_2$ and put at 38.7° C. Twice a day the cultures were transferred to 50 ml tissue culture tubes (Falcon) and centrifuged (400 g, 5', 4° C.). Of each culture 25 ml of the supernatant was collected, and replaced by fresh Babesia medium, prewarmed in a 37° C. waterbath. The cultures were gassed and incubation resumed. Supernatants were collected at 48, 60 and 72 hours of culture, pooled and concentrated to one-tenth the original using a tangential flow apparatus (Millipore) with a filter of 10 kD cutoff.

Vaccine formulations

Vaccines were obtained from the supernatant of Babesia cultures and contained one ml of concentrated supernatant of a culture of $2.10^8$ parasited erythrocytes per ml. Saponin (Quil A$^{(R)}$, Superfos) was added to a final concentration of 0.5 mg/ml.

Combination vaccines were composed by mixing one ml of concentrated supernatant of two different cultures to a total volume of 2 ml.

Saponin adjuvant control was obtained by diluting saponin in physiological salt solution to a concentration of 0.5 mg/ml.

Vaccination

Groups of five dogs were formed assuring an even distribution of litter and sex. Serum was collected prior to vaccination, and at weekly intervals during the whole experimental period (i.e. vaccination and challenge). Animals received a priming injection with vaccine and three weeks later a booster injection, subcutaneously.

Antibody titres (SELISA)

Antibody titres against parasited erythrocytes were determined using the slide-ELISA technique described earlier (Schetters et al., 1992). In short, serum dilutions are incubated on acetone-fixed blood smears of Babesia canis infected dogs. The immunoglobulin bound is visualised using a biotin-streptavidin-peroxidase detection system. Twofold serial dilutions are tested and titres are expressed as the last dilution step which gave a positive reaction (blue stain).

Clinical examination

After challenge infection all experimental animals were examined daily for clinical signs. Special attention was given to behaviour, spleen size, size of lymph nodes, colour of the mucous membrane of the eyelid, and the capillary refill time. The clinical score was determined as described earlier (Schetters et al., 1994). Dogs that had to be chemotherapeutically treated were given the maximal clinical score (=6). Chemotherapeutic treatment was considered when the health condition of the animal rapidly deteriorated. Dogs were injected with 0.6 ml Imizol (Pitman-Moore, Coopers) for two consecutive days. Within three days after this treatment no parasites are detectable in the peripheral blood.

Results

Example 1

Vaccinations with *B. c. canis*

Groups of five dogs were vaccinated with Intervet *B. c. canis* A vaccine as prepared above and subsequently challenged with homologous or heterologous parasites. After priming and boosting all animals showed antibody responses against parasitised erythrocytes. The mean antibody titre of the two vaccinated groups was comparable (FIG. 1). Upon challenge infection both groups of vaccinated animals exhibited slight decreases of antibody titres against parasitised erythrocytes. In both groups the antibody response was boosted by challenge infection. There was a one to two day difference between these booster responses; animals challenged with homologous parasites responding earlier (day 3–4) than those challenged with heterologous parasites (day 5).

Figure 2:
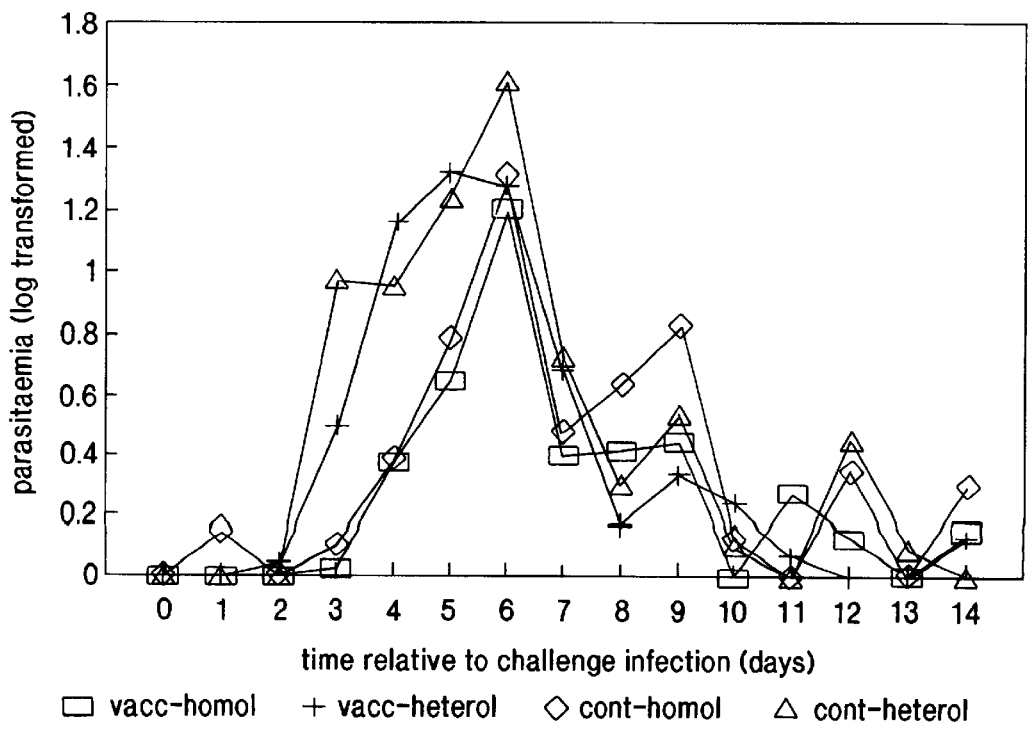
FIG. 2. The effect of vaccination with a monovalent vaccine on parasitaemia after homologous or heterologous challenge infection. Data represent the mean values of groups of animals and are log transformed.

Vaccination did not affect the course of parasitaemia after challenge infection irrespective of the parasite isolate used (FIG. 2). The prepatent period was two days, thereafter parasites were observed in the blood, and parasitaemia peaked at day 6 after infection. After that period of time parasitaemia declined, following an irregular pattern. Clear recrudescences were not observed, although there was a tendency of increased parasitaemia at days 9 and 12 of infection. In general, animals challenged with *B. c. canis* B parasites suffered from higher parasitaemias as compared to those infected with *B. c. canis* A parasites (Table I). None of the vaccinated animals that were challenged with homologous parasites required chemotherapeutical treatment. In contrast, in each of the other groups two out of five animals had to be treated for severe life-threatening babesiosis.

Figure 3:
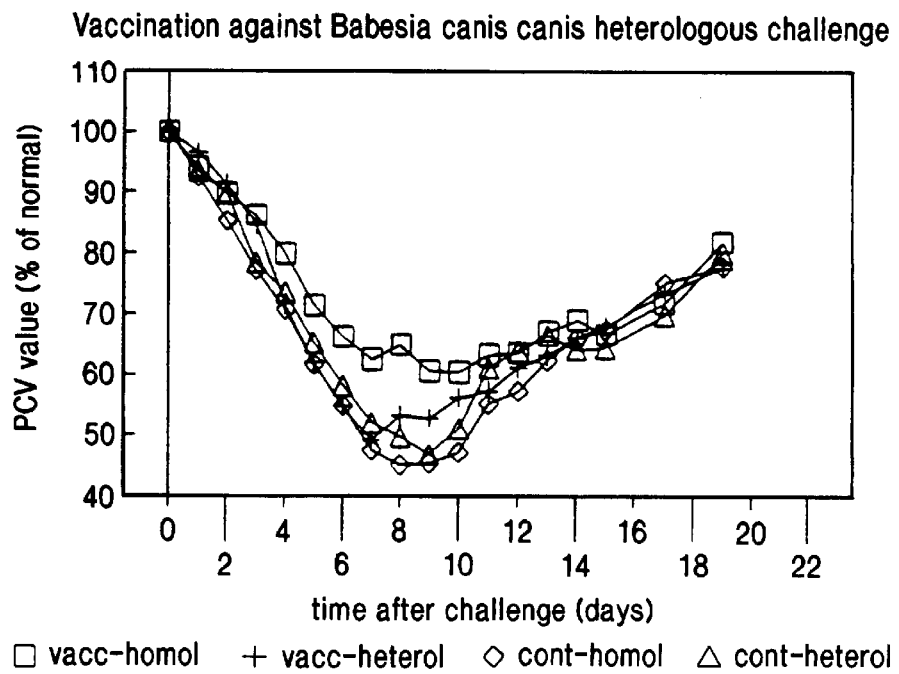
FIG. 3. The effect of vaccination with a monovalent vaccine on the peripheral red blood cell number after homologous or heterologous challenge infection. Data are expressed as packed cell values (PCV) and represent the mean value of groups of animals. Animals that were chemotherapeutically treated were from that day on omitted from the group.

All animals (vaccinated or not) suffered from anaemia as a result of challenge infection (FIG. 3). The first four days after infection the slope of the haematocrit values of the vaccinated animals was less steep than that of controls. From day 5 after infection onwards, the vaccinated animals that were challenged with homologous parasites diverted from the other animals, and from day 7 onwards there was no further decrease of haematocrit values in this group. Vaccinated animals that were challenged with heterologous parasites also showed signs of recovery from day 7 onwards. The haematocrit values of animals that had received adjuvant alone dropped further for another two days. At that time point there was an initially rapid increase of haematocrit values, followed by a period of more gradual recovery from day 11–12. When the maximal decrease of PCV for each individual animal was calculated it appeared that significantly less decreased values were observed in vaccinated animals that had experienced a homologous challenge infection. This was not found for the vaccinated animals that were challenged with heterologous parasites (Table I).

From this it follows that from vaccination with antigens of a particular subspecies of Babesia canis no protection against heterologous infection can be obtained.

Example 2
Dose-Response Relationship

Figure 4:
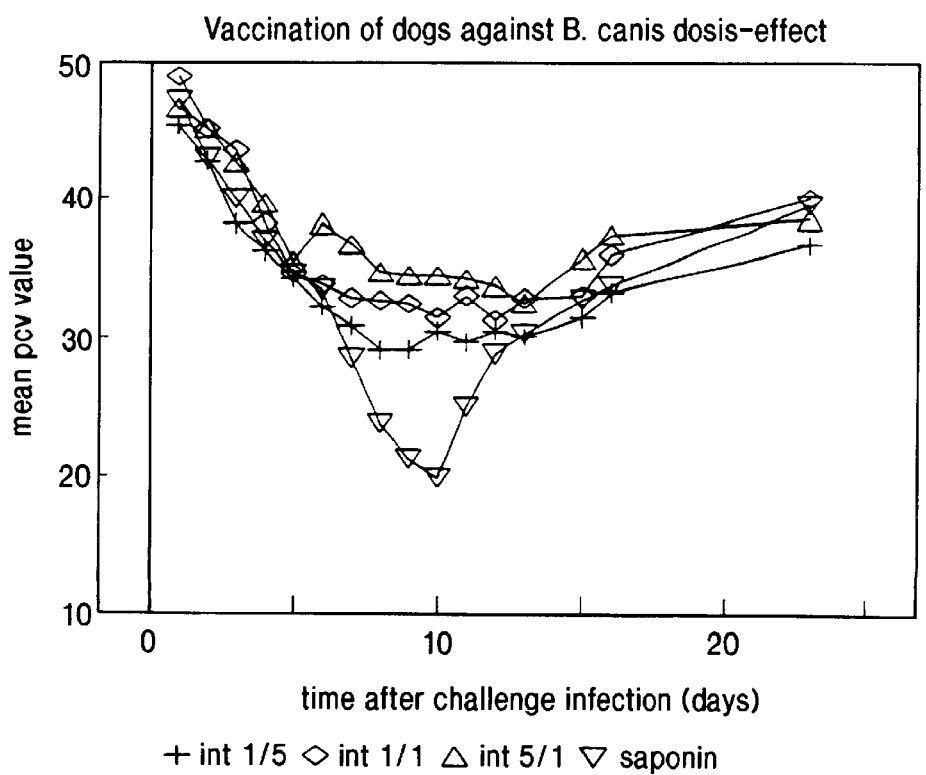
FIG. 4. The effect of different doses of monovalent vaccine on the peripheral red blood cell number after homologous challenge infection. Data are expressed as packed cell values (PCV) and represent the mean value of groups of animals. No animals were chemotherapeutically treated.

Groups of five dogs were vaccinated with three different doses of vaccine prepared from cultures of B. c. canis isolate A. The three doses were: normal dose, a 5× diluted and a 5× concentrated dose. The amount of adjuvant used was the same for every injection (1 mg Quil A/dose). Animals were vaccinated twice, with a three week interval. Three weeks after the booster injection animals were challenged with homologous parasites. It appeared that the animals vaccinated with the highest amount of antigen were best protected (FIG. 4 and Table II), although differences were small.

Thus, there is a broad range of antigen concentration which yields comparable levels of protection after vaccination.

Example 3
Vaccination With B. c. rossi and Heterologous Challenge

Groups of three dogs were vaccinated with a monovalent vaccine prepared from B. c. rossi culture supernatants. Animals received two injections, three weeks apart. Three weeks after the booster injection they were challenged with $2.10^6$ infected erythrocytes from B. c. canis isolate B. Animals had to be treated for severe clinical babesiosis at day 7 after challenge infection. The maximal decrease of PCV value was at that time 48.5 (12.0) and was not measured further because the animals received chemotherapeutical treatment. At that time the antibody titer was 4.0 as measured by slide-ELISA. In this experiment no control infections were carried out.

Figure 4A:
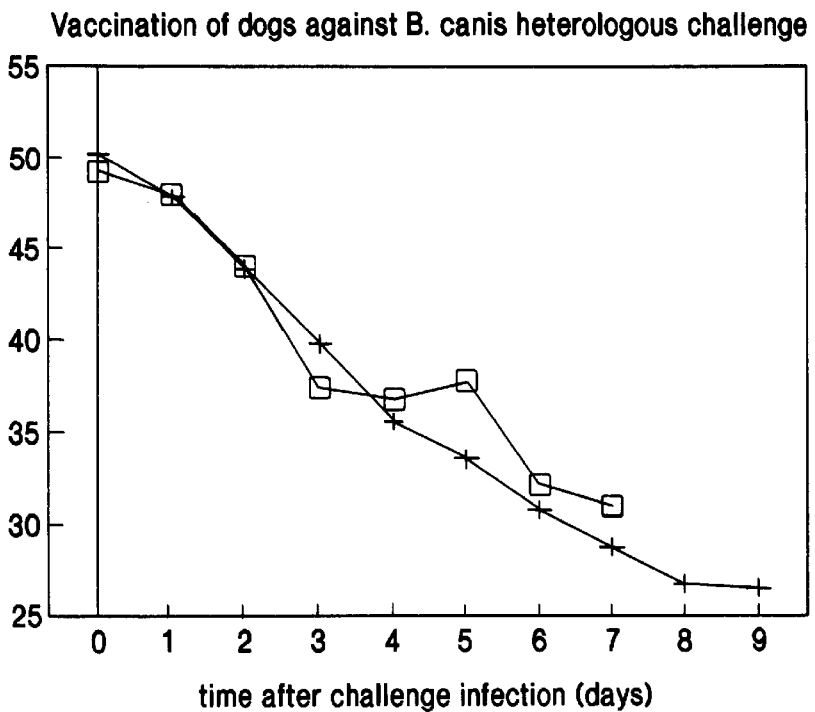
FIG. 4a. The effect of vaccination with monovalent *B. c. rossi* on the PCV value of dogs after challenge infection with heterologous *B. c. canis* B parasites. Data are expressed as packed cell values and represent the mean value of groups of animals. Animals that were chemotherapeutically treated were from that day on omitted from the group.

In a second experiment, groups of five dogs were vaccinated four times with three week intervals using a monovalent vaccine prepared of B. c. rossi culture supernatants. Upon vaccination the animals developed antibodies against B. canis parasites. After challenge infection with heterologous B. c. canis parasites it appeared that although there appeared to be an initial effects on the dynamics of the PCV values (slightly less decrease three to four days after challenge infection; see FIG. 4a), all animals had to be treated chemotherapeutically to prevent death.

From these experiments follows that vaccination with B. c. rossi alone does not give protection against heterologous challenges.

Example 4
Vaccination With a Combination Vaccine Based on Antigens from Culture Supernatants of B. c. canis Isolate A and B. c. rossi Groups of five dogs were vaccinated with a vaccine preparation based on antigens from B. c. canis isolate A culture and B. C. rossi culture. Of each of the components one dose was administered (the animals thus receiving a double antigen dose). Animals were injected twice, three weeks apart. Three weeks after the booster injection animals were challenged with heterologous parasites (B. c. canis isolate B).

Figure 5:
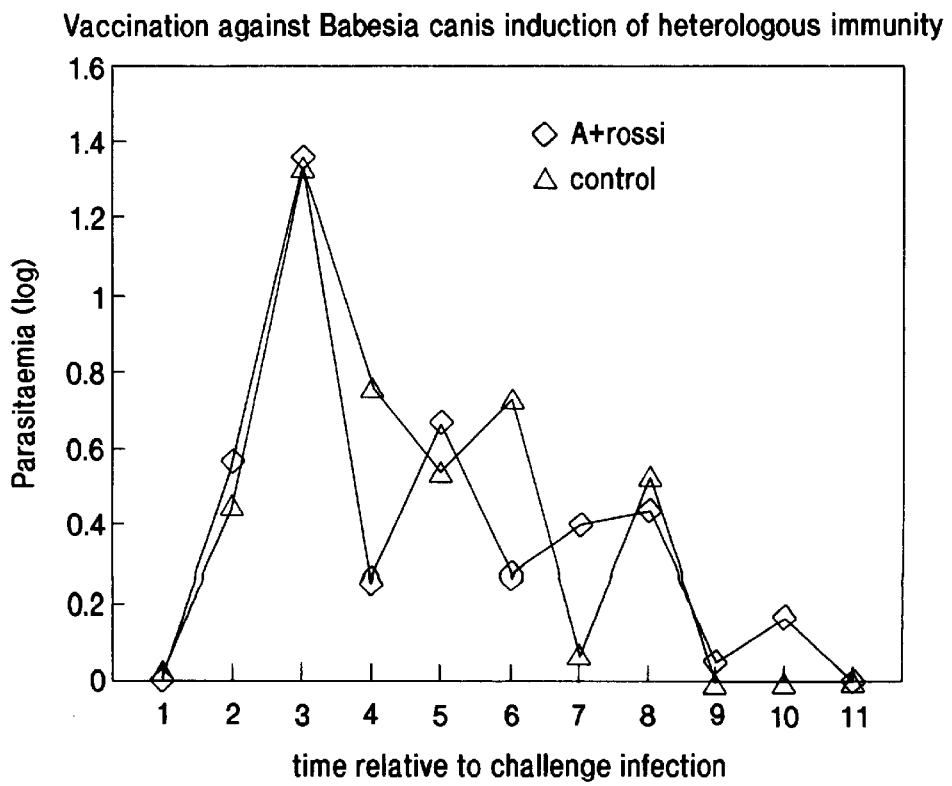
FIG. 5. The effect of vaccination with a combination vaccine on parasitaemia after challenge infection. Data represent the mean values of groups of animals, and are log transformed.

Vaccination did not affect the course of infection significantly (FIG. 5). The prepatent period was one day for both groups of animals. Parasitaemia increased rapidly, peaked at day three after infection, and subsequently declined. By day 11 parasitaemia was undetectable in both groups.

Vaccination induced antibodies against parasitised erythrocytes. The antibody titre of pooled plasma was 6 at the time of challenge infection (FIG. 6). After challenge infection the antibody titre dropped, but from day four onwards increased rapidly to levels of about 8. Importantly, this type of response was comparable to the response found after homologous challenge infections (supra, FIG. 1), indicating that vaccination with the combination vaccine provoked an effective memory response upon heterologous challenge infection.

Both groups of animals suffered from anaemia after challenge infection. The PCV value dropped the first four days in an identical manner (FIG. 7). From that day onwards the PCV value from the vaccinated animals did not drop significantly anymore. This coincided with the onset of the memory antibody response (FIG. 6). PCV values of the control animals decreased further, and the animals had to be treated chemotherapeutically. The maximal decrease of PCV value of the vaccinated group was significantly less than that of the control group (Table III). The dynamics of the PCV values of the vaccinated animals resembled that of vaccinated animals that were challenged with homologous parasites (FIG. 3). No clinical scores were obtained.

It appeared that the PCV drop of vaccinated dogs was significantly less (42.1±5.5) than controls (53.1±4.5), see also FIG. 5.

TABLE I

The effect of vaccination with Intervet canis A preparations on the haematocrit, parasitic load and clinical score values after challenge with Babesia canis canis isolate A or Babesia canis canis isolate B parasites.

| Treatment | Challenge infection | Max decr PCV[a] | Parasitic load | Max clin score |
|---|---|---|---|---|
| Intervet canis A | canis A | 44.9 (5.3) | 4.0 (1.2) | 2.6 (1.1) |
| Control | canis A | 60.6 (12.1) | 5.4 (1.5) | 4.0 (1.9) |
| Intervet canis A | canis B | 54.7 (10.1) | 5.9 (1.5) | 4.1 (2.0) |
| Control | canis B | 55.6 (10.7) | 7.0 (1.3) | 4.1 (1.9) |

[a]Data represent the group mean values (±sd).

TABLE II

The effect of vaccination with different doses of Intervet canis A preparations on the haematocrit, antibody titre and clinical score values after challenge with Babesia canis canis isolate A.

| Treatment | Challenge infection | Max decr PCV[a] | antibody titre | Max clin score |
|---|---|---|---|---|
| Antigen 1/5 | canis A | 42.0 (10.1) | 5.0 (0.7) | 2.3 (1.1) |
| Antigen 1/1 | canis A | 39.5 (3.5) | 7.0 (0.7) | 1.7 (0.9) |
| Antigen 5/1 | canis A | 35.1 (7.3) | 7.3 (0.5) | 1.6 (1.0) |
| Control Quil A | canis A | 62.2 (8.0) | 1.2 (0.5) | 4.4 (1.7) |

[a]Data represent the group mean values (±sd).

TABLE III

The effect of vaccination with a combination vaccine preparation on the hematocrit and antibody titre after challenge with Babesia canis canis isolate A Parasites.

| Treatment | Challenge infection | Max decr PCV[a] | Antibody titre[b] |
|---|---|---|---|
| Combination | canis A | 42.1 (5.5) | 6.0 |
| Adjuvant only | canis A | 53.1 (4.5) | 1.0 |

[a]Data represent the group mean values (±sd).
[b]titre measured from pooled serum. No sd available.

REFERENCES

Basson, P. A. and Pinnaar, J. G. (1965) Canine babesiosis: a report on the pathology of three cases with special reference to the 'cerebral' form. J. South Afric. Med. Ass. 36, 333.

Callow, L. L. and Dalgliesh, R. J. (1982) Immunity and immunopathology in babesiosis. In: Immunology of parasitic infections. Cohen, S. and Warren, K. (eds.) Blackwell Scientific Publ., Oxford, pp. 475.

Fisher, W. and Scheideman, H. (1920) Klinisches und Histologische Untersuchungen über Hunde Babesiose. Zentralbl. f. Bakt. Parasit. Infekt. U. Hygiene, Originale 84, 35.

Jacquier, C. (1973) Piroplasmose canine: polymorphisme clinique. Schweiz. Arch. f. Tierheilk. 115, 121.

Jarra, W. and Brown, K. N., (1985) Parasite Immunol. 7, 595

Lepetit, C. (1988) Piroplasmose canine et vaccination Pirodog. Thèse, Ecole Nationale Veterinaire de Nantes.

Malherbe, W. D. and parkin, B. S. (1951) Atypical symptomology in *Babesia canis* infection. J. South Afric. Vet. Med. Ass. 22, 25.

Moore, D. J. and Williams, M. C. (1979) Disseminated intravascular coagulation: a complication of *Babesia canis* infection in the dog. J. South Afr. Vet. Ass. 50, 265.

Nuttal, G. H. F. (1904) Canine piroplasmosis.

Ristic, M. and Montenegro-James, S. (1988) In: Babesiosis of domestic animals and man. Ed: Ristic, M. CRC Press Inc. Boca Raton, Fla., pp. 163

Schetters, Th. P. M. et al. (1992) Vaccination of dogs against *Babesia canis* infection using antigens from in vitro culture. Parasite Immunol. 14, 295–305.

Schetters, Th. P. M. et al. (1994) Vaccination of dogs against *Babesia canis* infection with emphasis on clinical babesiosis. Vet. Parasitol. 52(3–4), 219–233.

Schetters, Th. P. M. et al. (1995) Strain variation limits protective activity of vaccines based on soluble *Babesia canis* antigens. Parasite Immunol, 17, xx—xx.

Sibinovic, K. H. et al. (1967) A study of some of the physical, chemical and serological properties of antigens from sera of horses, dogs and rats with acute babesiosis. J. Parasitol. 53, 919.

Uilenberg, G. et al. (1989) Three groups of *Babesia canis* distinguished and a proposal for nomenclature. Vet. Quart. 11, 33.

I claim:

1. A method for protecting a dog against babesisois with a heterologous vaccine, said babesisois caused by a strain of B. c. canis which is not included in said vaccine, comprising the step of administering said vaccine which contains soluble antigens from B. canis rossi and from at least one strain of B. c. canis that is not the strain against which protection is being sought, in immunogenically effective amounts, and a pharmaceutically acceptable carrier or adjuvant.

2. The method of claim 1 for protecting a dog against babesiois caused by B. c. canis strain B, comprising the step of administering a vaccine comprising soluble antigens from B. canis rossi and at least one strain of B. c. canis, in immunogenicalLy effective amounts, and a pharmaceutically acceptable carrier or adjuvant, wherein said vaccine does not contain B. c. canis strain B.

3. The method of claim 2, wherein said babesisois is caused by B. c. canis strain B, and said vaccine comprises soluble antigens from B. canis rossi and from B. c. canis strain A but not B. c. canis strain B.

* * * * *